US012788708B2

(12) United States Patent
Rossignol-Castera et al.

(10) Patent No.: US 12,788,708 B2
(45) Date of Patent: *Nov. 10, 2026

(54) PLANT DERIVED ACTIVE INGREDIENT COMPRISING PLANT EXTRACTS

(71) Applicant: DONCAB, Aix-en-Provence (FR)

(72) Inventors: Anne Rossignol-Castera, Lunel (FR); Annabelle L'Hermitte, Beaulieu (FR); Gregoire Clot, Aix-en-Provence (FR)

(73) Assignee: DONCAB, Aix-en-Provence (FR)

( * ) Notice: Subject to any disclaimer, the term of this patent is extended or adjusted under 35 U.S.C. 154(b) by 484 days.

This patent is subject to a terminal disclaimer.

(21) Appl. No.: 18/221,163

(22) Filed: Jul. 12, 2023

(65) Prior Publication Data

US 2025/0017845 A1 Jan. 16, 2025

(51) Int. Cl.

*A61K 36/00* (2006.01)
*A61K 8/9789* (2017.01)
*A61K 36/63* (2006.01)
*A61K 36/73* (2006.01)
*A61Q 19/08* (2006.01)

(52) U.S. Cl.

CPC ............ *A61K 8/9789* (2017.08); *A61K 36/63* (2013.01); *A61K 36/73* (2013.01); *A61Q 19/08* (2013.01); *A61K 2236/37* (2013.01); *A61K 2800/805* (2013.01)

(58) Field of Classification Search

None
See application file for complete search history.

(56) References Cited

U.S. PATENT DOCUMENTS 11,684,563 B2 * 6/2023 Rossignol-Castera ...................... A61K 8/9789 424/765
2008/0241084 A1 * 10/2008 Siddiqui ................ A61K 36/45 424/62
2022/0218592 A1 * 7/2022 Rossignol-Castera ...................... A61K 8/9789

FOREIGN PATENT DOCUMENTS

| | | | |
|---|---|---|---|
| FR | 2943684 | A1 | 10/2010 |
| GB | 501732 | A | 2/1939 |
| JP | H08104646 | A | 4/1996 |
| JP | H1171291 | A | 3/1999 |
| JP | 2012206957 | A | 10/2012 |
| WO | 2009122045 | A2 | 10/2009 |

OTHER PUBLICATIONS

Jabeur et al., "Contribution of Phenolic Composition to the Antioxidant, Anti-Inflammatory and Antitumor Potential of *Equisetum giganteum* L. and Tilia Platyphyllos Scop." Food Function, Royal Society of Chemistry, 2017, pp. 1-32.
Kim et al., "Chemical Constituents of Tilia Taquetti Leaves and Their Inhibition of MMP-1 Expression and Elastase Activities," Natural Product Communications, 2004, vol. 9, No. 12, pp. 1683-1685.
Yamamoto et al., "Identification of Quince Varieties Using SSR Markers Developed from Pear and Apple," Breeding Science, 2004, vol. 54, pp. 239-244.
Nov. 3, 2022 Office Action issued in U.S. Appl. No. 17/149,368.
Feb. 13, 2023 Notice of Allowance issued in U.S. Appl. No. 17/149,368.
U.S. Appl. No. 17/149,368, filed in the name of Rossignol-Castera et al., on Jan. 14, 2021.

* cited by examiner

*Primary Examiner* — Russell G Fiebig
(74) *Attorney, Agent, or Firm* — Oliff PLC

(57) ABSTRACT

A plant derived active ingredient and a cosmetic and a drug composition including the plant derived ingredient, the plant derived active ingredient including an extract from at least one plant of the gender *Olea*, an extract from at least one plant of the gender *Tilia* and/or an extract from at least one plant of the gender *Cydonia*.

15 Claims, 1 Drawing Sheet

VW=very weak; W=weak; M=moderate; FC= Fairly clear; C=clear; VC=very clear; S=strong

PLANT DERIVED ACTIVE INGREDIENT COMPRISING PLANT EXTRACTS

PRIOR ART

Plant extract are used since a long time for their benefits in cosmetics or pharmaceuticals applications.

Linden is a plant of the gender *Tilia. Tilia platyphyllos* is a tree frequently encountered in middle and eastern regions of France. In the ancient Gaul, linden was the traditional tree in center of the village under which the inhabitants used to gather.

Linden dried bracts are commonly consumed in herbal teas: antispasmodic, sedative, digestive, slightly diuretic, expectorant and perspirant. The dried sapwood is consumed as a decoction as a drainer of the liver and kidneys, especially in case of uric acid overload, renal or biliary lithiasis and digestive spasms. Its charcoal has been used in medicine for the treatment of digestive problems, it can also sanitize burns.

For 150 years, the Linden (*Tilia platyphyllos*) and the Baronnies Provençales have shared a common history. Inhabitants, farmers and merchants have written some fine pages in the domestication of this tree, while responding to the growing demand from the perfume industry, and later from herbalists. Drawing on a natural heritage that had been present for millennia, they selected varieties from wild lime trees to improve the quality and quantity produced.

In this region, the *Tilia platyphyllos*, also called "tilleul muscat" has a very specific genetic heritage due to low levels of crossbreeding.

One hundred and fifty years of history made up of discoveries, innovations, but also conflicts or failures. But even today, the *Tilia platyphyllos* is, a symbol of loyalty and hospitality, arouses the same passion.

For several years now, the Parc naturel régional des Baronnies provençales, in partnership with several stakeholders and thanks to various funding sources (Direction régionale des Affaires Culturelles Auvergne-Rhône-Alpes, Europe under the Leader program) has been seeking to gain a better understanding of this history and heritage, to use it as a springboard to revive *Tilia platyphyllos* production.

JPH1171291 discloses an aqueous extract od a plant of the gender *Tilia* as an immunoactivator.

I. Jabeur et al., Food Funct., 2017 discloses the antioxidant, anti-inflammatory and antitumor potentials of *Equisetum giganteum* L. and *Tilia platyphyllos* extracts.

Su Yeong Kim et al., Natural product communications, 2014, Vol. 9, No. 12, 16683-1685 discloses the effects of *Tilia* taquetii ethanolic extracts on inhibition of MMP-1 expression and elastase activities.

The Quince tree is a plant of the gender *Cydonia. Cydonia oblonga* is a tree native to Asia Minor, the Caucasus, and the Caspian region. Quince is an ancient fruit, its cultivation preceded that of the apple. Among the ancient Greeks, the quince was a ritual gift for weddings.

Quince extracts has several biological activities like antimicrobial (skin of the fruit), antioxidant (leaves and fruits), healing (seeds).

GB501732 discloses a cosmetic composition in an emulsion form comprising olive oil and quince seed extract.

JP20122206957 discloses a collagen production promoter made from an extract of a *Cydonia oblonga* seed.

The olive tree is a plant of the gender *Olea. Olea* Europa is found in the Mediterranean region of Europe, Asia, and North Africa. Symbol of longevity and hope, it is reputed to be eternal throughout the Mediterranean region, it is also a symbol of peace, reconciliation, victory, and strength.

Olive extracts are known to have antimicrobial and antioxidant properties.

WO2009122045 discloses the use of olive oil extract to control skin aging.

US2008/0241084 A1 discloses a cleansing foam comprising *Tilia cordata* and *Olea europaea* but does not disclose the particular extraction method and thus is a different product.

JP08104646 A discloses composition comprising *Tilia platyphyllos* but does not disclose the particular extraction method and thus is a different product.

Thanks to the particular extraction method, the plant derived active ingredient according to the invention has surprisingly demonstrated antioxidant effect and effect on the collagen synthesis in the skin making it especially interesting as cosmetic active ingredient.

DETAILED DESCRIPTION OF THE INVENTION

Figure 1:
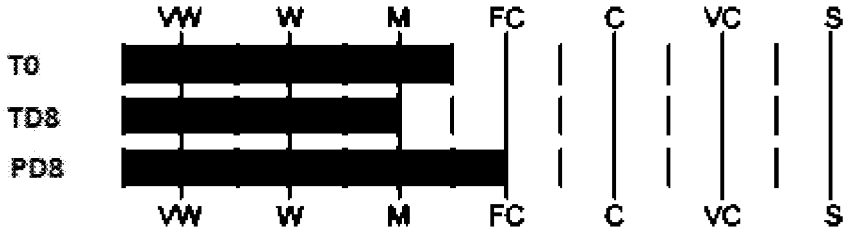
FIG. 1 illustrates the staining strength of collagen I in the papillary dermis of all the batches of human skin explants.

The present invention is about a plant derived active ingredient comprising:

An extract from at least one plant of the gender *Olea,*

An extract from at least one plant of the gender *Tilia* and/or an extract from at least one plant of the gender *Cydonia* herein the plant derived ingredient is obtained by an extraction method comprising:

a) mixing and impregnating at least one plant of the gender *Tilia* and/or at least one plant of the gender *Cydonia* with the extract from at least one plant of the gender *Olea* in an oily form at a temperature which is greater than the melting point of said extract from at least one plant of the gender *Olea,* b) heating to a temperature between 80 to 200° C., c) microdispersing said extract from at least one plant of the gender *Tilia* and/or said extract from at least one plant of the gender *Cydonia* into said extract from at least one plant of the gender *Olea,* d) separating the oily content by centrifugation and/or filtration.

In an embodiment, the at least one plant of the gender *Olea* is selected from the group consisting of *Olea europaea, Olea paniculata, Olea ambrensis, Olea capensis, Olea undulata, Olea woodiana, Olea lancea, Olea caudatilimba, Olea brachiata, Olea guangxiensis, Olea hainanensis, Olea laxiflora, Olea neriifolia, Olea parvilimba, Olea rosea, Olea salicifolia, Olea tetragonoclada, Olea tsoongii, Olea chrysophylla, Olea exasperata, Olea hochstetteri, Olea welwitschii,* alone or in combination.

In a preferred embodiment, the at least one plant of the gender *Olea* is *Olea europaea.*

In an embodiment, the at least one plant of the gender *Tilia* is selected from the group consisting of *Tilia platyphyllos, Tilia americana, Tilia heterophylla, Tilia miqueliana, Tilia amurensis, Tilia mongolica, Tilia begoniifolia, Tilia monticola, Tilia caroliniana, Tilia nasczokinii, Tilia neglecta, Tilia chenmoui, Tilia nobilis, Tilia occidentalis,*

*Tilia chinensis, Tilia chingiana, Tilia cordata, Tilia orbicularis, Tilia oliveri, Tilia croizatii, Tilia paucicostata, Tilia petiolaris, Tilia dasystyla, Tilia endochrysea, Tilia floridana, Tilia henryana, Tilia heterophylla, Tilia hillieri, Tilia hupehensis, Tilia insularis, Tilia intonsa, Tilia japonica, Tilia kiusiana, Tilia koreana, Tilia ledebourii, Tilia mandshurica, Tilia maximowicziana, Tilia mexicana, Tilia rubra, Tilia sibirica, Tilia taquetii, Tilia tuan, Tilia tomentosa, Tilia varsaviensis, Tilia zaeskania*, alone or in combination.

In a preferred embodiment, the at least one plant of the gender *Tilia* is *Tilia platyphyllos*.

In a preferred embodiment, the at least one plant of the gender *Tilia* is *Tilia platyphyllos* is from the region of "Baronnies Provençales" in France.

In an embodiment, the at least one plant of the gender *Cydonia* is *Cydonia oblonga*.

*Cydonia oblonga* is also known as *Cydonia* vulgaris or *Pyrus Cydonia*. The *Cydonia oblonga* plant used herein can be of various varieties alone or in combination, for example it can be one of the varieties listed and identified in the publication: Yamamoto et al.; Breeding Science; 54:239-244 (2004)

In an embodiment, the plant extracts originate from leaves, fruits, flowers, roots, seeds, stems, bark, or wood of said plants.

In a preferred embodiment, the extract from at least one plant of the gender *Olea* originates from the fruits of said plant.

In a preferred embodiment, the extract from at least one plant of the gender *Tilia* originates from the flowers of said plant.

In an embodiment, the extract from at least one plant of the gender *Cydonia* originates from the leaves of said plant.

An extract of *Olea europaea* can comprise numerous phenolic compounds as for example phenolic alcohols (tyrosol, hydroxytyrosol, verbascoide), phenolic acids (caffeic acid, vanillic acid), flavonoids (apigenin, luteolin, rutin), secoiridoids (oleuropein, ligstroside), lignanes (cycloolivil).

In an embodiment, the extract from at least one plant of the gender *Olea* comprises from 0.001 to 1% by weight of polyphenols in relation to the total weight of the extract.

In an embodiment, the extract from at least one plant of the gender *Olea* comprises from 0.005 to 0.5% by weight of polyphenols in relation to the total weight of the extract.

In an embodiment, the extract from at least one plant of the gender *Olea* comprises from 0.01 to 0.1% by weight of polyphenols in relation to the total weight of the extract.

In an embodiment, the extract from at least one plant of the gender *Olea* comprises a polyphenols concentration from 50 to 5000 mg/kg.

In an embodiment, the extract from at least one plant of the gender *Olea* comprises a polyphenols concentration from 100 to 3000 mg/kg.

In an embodiment, the extract from at least one plant of the gender *Olea* comprises a polyphenols concentration from 500 to 1000 mg/kg.

The concentration in polyphenols is calculated in mg/kg oleuropein equivalent in this application.

An extract of *Tilia platyphyllos* can comprise at least 33 different polyphenolic compounds: 3 phenolic acids and 30 flavonoids mainly quercetin and kaempferol derivatives. It further comprises carotenoids as for example lutein and β-carotene.

In an embodiment, the extract from at least one plant of the gender *Tilia* comprises from 1 to 30% by weight of polyphenols in relation to the total weight of the extract.

In an embodiment, the extract from at least one plant of the gender *Tilia* comprises from 5 to 25% by weight of polyphenols in relation to the total weight of the extract.

In an embodiment, the extract from at least one plant of the gender *Tilia* comprises from 10 to 20% by weight of polyphenols in relation to the total weight of the extract.

In an embodiment, the extract from at least one plant of the gender *Tilia* comprises a polyphenols concentration from 10,000 to 500,000 mg/kg.

In an embodiment, the extract from at least one plant of the gender *Tilia* comprises a polyphenols concentration from 50,000 to 300,000 mg/kg.

In an embodiment, the extract from at least one plant of the gender *Tilia* comprises a polyphenols concentration from 100,000 to 200,000 mg/kg.

An extract of *Cydonia oblonga* can comprise numerous phenolic compounds as for example flavonoids, glycosylated flavonoids, chlorogenic acids. It further comprises organic acids, sugars, amino acids, fatty acid esters, triterpene compounds, carotenoids.

In an embodiment, the extract from at least one plant of the gender *Cydonia* comprises from 10 to 60% by weight of polyphenols in relation to the total weight of the extract.

In an embodiment, the extract from at least one plant of the gender *Cydonia* comprises from 20 to 50% by weight of polyphenols in relation to the total weight of the extract.

In an embodiment, the extract from at least one plant of the gender *Cydonia* comprises from 30 to 40% by weight of polyphenols in relation to the total weight of the extract.

In an embodiment, the extract from at least one plant of the gender *Cydonia* comprises a polyphenols concentration from 100,000 to 600,000 mg/kg.

In an embodiment, the extract from at least one plant of the gender *Cydonia* comprises a polyphenols concentration from 200,000 to 500,000 mg/kg.

In an embodiment, the extract from at least one plant of the gender *Cydonia* comprises a polyphenols concentration from 300,000 to 400,000 mg/kg.

In an embodiment, the plant derived active ingredient according to the invention further comprises at least one surfactant.

In an embodiment, the at least one surfactant is a water in oil surfactant.

This surfactant is preferentially a "polyglyceryl" type fatty acid ester.

In an embodiment, the at least one water in oil surfactant is selected from the group consisting of polyglyceryl-4 oleate, polyglyceryl-3 diisostearate, polyglyceryl-6 dioleate, polyglyceryl-3 caprate, glycerol stearate, or phospholipids (for example lecithins), alone or in combination.

In an embodiment, the mass ratio between the extract from at least one plant of the gender *Tilia* and/or the extract from at least one plant of the gender *Cydonia* and the extract from at least one plant of the gender *Olea* is from 1:2 to 1:10 and preferably from 1:3 to 1:5.

When used together, the mass ratio between the extract from at least one plant of the gender *Cydonia* and the extract from at least one plant of the gender *Tilia* is from 1:2 to 1:10, preferably from 1:3 to 1:5, and most preferably equal to 1:4.

In an embodiment, the plant derived active ingredient according to the invention comprises a polyphenols concentration from 200 to 20,000 mg/kg.

In an embodiment, the plant derived active ingredient according to the invention comprises a polyphenols concentration from 3,000 to 16,000 mg/kg.

In an embodiment, the plant derived active ingredient according to the invention comprises a polyphenols concentration from 8,000 to 12,000 mg/kg.

In a preferred embodiment, the plant derived active ingredient according to the invention is in an oily form.

In another embodiment, the plant derived active ingredient according to the invention is in an emulsion form.

A plant extract can be obtained from different solvents.

Organic solvents such as hexane or acetone present either a health risk or an environmental risk. Ethanol is considered a skin irritant. Water is a green solvent but requires the addition of chemical preservatives to ensure microbiological stability. These disadvantages are not encountered with the use of vegetable oil as an extraction solvent.

The plant derived active ingredient according to the invention is preferably manufactured by the method disclosed in the patent FR2943684.

Vegetable oils are in fact green solvents, derived from renewable agricultural sources and have no impact on the environment and health. Vegetable oils are neither irritating nor allergenic on the skin. They do not require any chemical preservatives or other additives because they do not present any microbiological risk. They naturally contain active compounds in the skin such as polyunsaturated fatty acids omega 3 or omega 6 or vitamin E.

In addition, oily extracts can be directly and easily formulated in an emulsion but also in an anhydrous cosmetic product, i.e. without an aqueous phase, or with a continuous fatty phase, such as an anti-ageing oily serum, a repairing care oil or a make-up.

Oily plant extracts therefore have many advantages over other forms of extracts.

In a preferred embodiment, at least one plant of the gender *Tilia* and/or at least one plant of the gender *Cydonia* is in a powder form in step a) of the extraction method.

In a preferred embodiment, step a), b) and/or c) of the extraction method is performed under an atmosphere which is depleted or essentially depleted in oxygen.

In a preferred embodiment, step b) of the extraction method is performed in less than 10 minutes.

In a preferred embodiment, step b) of the extraction method is performed by means of microwaves.

In a preferred embodiment, step c) of the extraction method is performed at a temperature which is greater than the melting point of said extract from at least one plant of the gender *Olea*.

In a preferred embodiment, step c) of the extraction method is performed at a temperature which is greater than the melting point of said extract from at least by means of ultrasonic cavitation treatment.

In a preferred embodiment, the plant derived active ingredient according to the invention is obtainable by means of an extraction method comprising the following steps:

e) mixing and impregnating at least one plant of the gender *Tilia* and/or at least one plant of the gender *Cydonia* in a powder form with the extract from at least one plant of the gender *Olea* in an oily form at a temperature which is greater than the melting point of said extract from at least one plant of the gender *Olea* and under an atmosphere which is depleted or essentially depleted in oxygen, f) heating to a temperature between 80 to 200° C. during less than 10 minutes by means of microwaves and under an atmosphere which is depleted or essentially depleted in oxygen, g) microdispersing said extract from at least one plant of the gender *Tilia* and/or said extract from at least one plant of the gender *Cydonia* into said extract from at least one plant of the gender *Olea* at a temperature which is greater than the melting point of said extract from at least one plant of the gender *Olea* and under an atmosphere which is depleted or essentially depleted in oxygen, by means of ultrasonic cavitation treatment, h) separating the oily content by centrifugation and/or filtration step c) being able to be implemented before, during or after step b).

In an embodiment, at step a) is added at least one surfactant acting as co-extractant, preferably a water in oil surfactant.

This surfactant is preferentially a "polyglyceryl" type fatty acid ester.

In an embodiment, the at least one water in oil surfactant is selected from the group consisting of polyglyceryl-4 oleate, polyglyceryl-3 diisostearate, polyglyceryl-6 dioleate, polyglyceryl-3 caprate, glycerol stearate, or phospholipids (for example lecithins), alone or in combination.

In an embodiment, said treatment by ultrasonic cavitation of step c) is carried out for a period between 2 and 30 minutes, at a cavitation frequency of less than 100 KHz.

In an embodiment, step a) and b) and c) are carried out under nitrogen atmosphere.

The present invention further concerns a cosmetic composition comprising the plant derived active ingredient according to the invention.

In an embodiment, the cosmetic composition according to the invention comprises from 0.1 to 10% by weight of said plant derived active ingredient in relation to the total weight of the composition.

In a preferred embodiment, the cosmetic composition according to the invention comprises from 1 to 5% by weight of said plant derived active ingredient in relation to the total weight of the composition.

In a particularly preferred embodiment, the cosmetic composition according to the invention comprises from 2 to 4% by weight of said plant derived active ingredient in relation to the total weight of the composition.

In an embodiment, the cosmetic composition according to the invention is in the form of a cream, a shampoo, a gel, an emulsion, a milk, a lotion, a serum, an ointment, a foam, an essence, an oil, a wax, a stick, a powder, encapsulated, an injectable solution, and more generally in all cosmetic products as defined in the EC Directive 1223/2009 relating to cosmetic products.

In an embodiment, the cosmetic composition according to the invention further comprises at least one excipient chosen from the group consisting of solvents, denaturants, humectants, perfumes, viscosity control agents, emulsifiers, surfactants, emollients, foam boosters, hair care agents, hydrotropes, skin care agents, fixing agents, emulsion stabilizers, gelling agents, antioxidants, preservatives, chelating agents, pH regulators, masking agents, film-forming agents, adsorbents, hair fixatives, oral hygiene agents, deodorants, cosmetic dyes, opacifiers, lipid restoratives, UV filters, UV absorbers, abrasive agents, anti-caking agents, fillers, cleaning agents, antifoaming agents, moisturizing agents, foaming agents, antistatic agents, plasticizing agents, antimicrobial agents, softening agents, emollients, toning agents, emulsion stabilizers, and binders, alone or in combination.

The present invention further concerns a drug composition comprising the plant derived active ingredient according to the invention.

In an embodiment, the drug composition according to the invention is in a pharmaceutical form selected from the group consisting of an oral form, injectable form, dermal form, rectal form, inhaled form.

In an embodiment, the drug composition according to the invention is in an oral form.

In an embodiment, the oral form is selected in the group consisting of a tablet, an effervescent tablet, a dispersable tablet, a sublingual tablet, a capsule, a syrup, an oral solution, a drinkable suspension.

In an embodiment, the drug composition according to the invention is in an injectable form.

In an embodiment, the drug composition according to the invention is in a dermal form.

In an embodiment, the dermal form is selected in the group consisting of an ointment, a lotion, a gel, a solution, patch.

In an embodiment, the drug composition according to the invention is in a rectal form.

In an embodiment, the drug composition according to the invention is in an inhaled form.

The present invention further concerns the use of the plant derived active ingredient according to the invention for the manufacture of a cosmetic composition.

The present invention further concerns the use of the plant derived active ingredient according to the invention for the manufacture of a drug composition.

The present invention further concerns the use of the plant derived active ingredient according to the invention for increase of collagen synthesis in a subject.

In an embodiment, collagen is type I collagen.

The present invention further concerns the use of the plant derived active ingredient according to the invention for decrease oxidative damages said cosmetic method comprising applying on the skin the plant derived active ingredient according to the invention or the cosmetic composition according to the invention.

The present invention further concerns a cosmetic method for decreasing skin ageing and/or increasing biomechanical properties of skin comprising firmness and/or elasticity said cosmetic method comprising applying on the skin the plant derived active ingredient according to the invention or the cosmetic composition according to the invention.

The present invention further concerns a cosmetic method for decreasing reducing skin symptoms caused by oxidative stress and/or pollution said cosmetic method comprising applying on the skin the plant derived active ingredient according to the invention or the cosmetic composition according to the invention.

The present invention further concerns a cosmetic method for increasing the radiance of the skin said cosmetic method comprising applying on the skin the plant derived active ingredient according to the invention or the cosmetic composition according to the invention.

The present invention further concerns a cosmetic method for decreasing skin ageing, increasing biomechanical properties of skin comprising firmness and/or elasticity, and/or reducing skin symptoms caused by oxidative stress and/or pollution, and/or increasing the radiance of the skin said cosmetic method comprising applying on the skin the plant derived active ingredient according to the invention or the cosmetic composition according to the invention.

EXAMPLES

Example 1: Manufacture of a Plant Derived Active Ingredient According to the Invention 80 g of flowering tops of *Tilia platyphyllos* plant and 20 g of leaves of *Cydonia oblonga* plant, are air-dried and then crushed at −80° C. with a knife mill for 1 min to obtain a fine, homogeneous powder. The average final particle size is between about 200 and 300 microns. The resulting powder is then mixed with 500 ml of *Olea europaea* oil.

Oily impregnation is carried out in a closed system for 2 hours after nitrogen bubbling and at room temperature.

The oily impregnation is followed by an intensified extraction carried out under nitrogen sweeping and the mixture is submitted to 800 watts of microwave power in 2×3 min. The maximum temperature reached is 145° C.

The last step is a micro-dispersion of plant powder conducted always under nitrogen sweeping and under an ultrasonic frequency of 20 kHz for 2×3 min.

Then the oil is separated by centrifugation at 5000 rpm for 5 min and then filtered.

The content of total phenolic compounds measured by the Ciocalteau FoNn method in oleuropein equivalent is 475 mg/kg for the oily extract obtained by the process.

Example 2: Manufacture of a Plant Derived Active Ingredient According to the Invention with Addition of Polyglyceryl-4 Oleate The process is equivalent as in the example 1 except that the plant powder is mixed with *Olea europaea* oil plus polyglyceryl-4 oleate acting as co-extractant.

The content of total phenolic compounds measured by the Ciocalteau FoNn method in oleuropein equivalent is 10,743 mg/kg, it represents a gain in polyphenols of +2162%, i.e. a concentration of phenols multiplied more than 22 times.

Example 3: Cosmetic Composition Comprising a Plant Derived Active Ingredient According to the Invention

TABLE 1

Facial oil composition comprising a plant derived active ingredient according to the invention.

| Ingredient (INCI name) | Percentage |
|---|---|
| SQUALANE | 34% |
| SIMMONDSIA CHINENSIS SEED OIL | 29% |
| CAMELINA SATIVA SEED OIL | 19.5% |
| PRUNUS ARMENIACA KERNEL OIL | 14.5% |
| Plant derived active ingredient according to the invention | 3% |

Example 4: Assessment of the Activity of a Plant Derived Active Ingredient According to the Invention on the Stimulation of Collagen I Synthesis on Human Living Skin Explants Ex Vivo Aim of the Study:

Evaluate a boost in the collagen I synthesis of a plant derived active ingredient according to the invention on human living skin explants ex vivo. The activity has been evaluated by a control of the cell viability after Masson's trichrome staining and an immunostaining of collagen I.

Material & Methods:

The study is scheduled on 8 days.

9 human skin explants of an average diameter of 12 mm (+/−1 mm) were prepared on an abdoplasty coming from a 65-year-old Caucasian woman with a phototype II. The explants were kept in survival in BEM culture medium (BIO-EC's Explants Medium) at 37° C. in a humid, 5% $CO_2$ atmosphere.

The plant derived active ingredient according to the invention (A) was diluted at 1% paraffin oil (product P) for the batch P. The diluted solution P was stored at 4° C., in the dark, during the study and well homogenized before each treatment. The explants were distributed into 3 batches.

TABLE 2

Distribution of the 9 human skin explants.

| Batches | Designation | Treatment | Number of explants | Sampling time |
|---|---|---|---|---|
| T0 | Control of the tissue | / | 3 | Day 0 |
| T | Blank batch | / | 3 | Day 8 |
| P | Product P | A at 1% | 3 | Day 8 |

The tested product P was applied topically based on 2 μl per explant (2 mg/cm²) and spread using a small spatula on day 0 (DO), D1, D4, D5, D6 and D7. The control explants T did not receive any treatment except the renewal of culture medium. The culture medium was half renewed (1 ml per well) on D1, D4 and D6.

On D0, the 3 explants from the batch TO were collected and cut in two parts. Half was fixed in buffered formalin solution and half was frozen at −80° C. On D8, 3 explants from all batches were collected and treated in the same way than in DO.

After fixation for 24 hours in buffered formalin, the samples were dehydrated and impregnated in paraffin using a Leica PEARL dehydration automat. The samples were embedded using a Leica EG 1160 embedding station. 5-μm-thick sections were made using a Leica RM 2125 Minot-type microtome, and the sections were mounted on Super-frose® histological glass slides. The frozen samples were cut into 7-pm-thick sections using a Leica CM 3050 cry-ostat. Sections were then mounted on Superfrost® plus silanized glass slides. The microscopical observations were realized using a Leica DMLB and an Olympus BX43 or BX63 microscope. Pictures were digitized with a numeric DP72 or DP74 Olympus camera with cellSens (Olympus) storing software.

The cell viability of the epidermal and dermal structures was assessed by microscopical observation of formalin-fixed paraffin embedded skin sections after Masson's trichrome staining, Goldner variant.

Collagen I immunostaining was performed on frozen sections with a polyclonal anti-collagen I antibody (Monosan, ref. PS047) diluted at 1:100 in PBS-BSA 0.3%-Tween 20 at 0.05% and incubated for 1 hour at room temperature and revealed by AlexaFluor488 (Lifetechnologies, ref. A11008). The nuclei were counterstained with propidium iodide. The immunostaining was performed using an automated slide processing system (Autostainer, Dako) and assessed by microscopical observation.

Results:

TABLE 3

Results of cell viability.

| Batch | Cell viability: Epidermis | Cell viability: Dermis |
|---|---|---|
| T0 | Good | Good |
| TD8 | Fairly Good | Good |
| PD8 | Fairly Good | Good |

On D0, on the blank batch TO, the cell viability is good in the epidermis and in the dermis. On D8, on the blank batch TD8, the cell viability is good in the epidermis and good in the dermis. The product P induces no modification.

The staining of collagen I in the papillary dermis of all the batches is shown in FIG. 1.

On day 0, on the blank batch TO, the staining of collagen I is moderate to clear in the papillary dermis. On day 8, on the blank batch TD8, collagen I expression is moderate in the papillary dermis. The product P induces a moderate increase.

Conclusion:

The product P stimulates the expression of collagen I on human living skin explants ex vivo after 8 days of treatment, so the plant derived active ingredient according to the invention induces a boost in collagen I synthesis.

Example 5: Image Analysis of Collagen I Immunostaining Performed in Example 1

Image Analysis Method:

The images analyses were performed on all the images of each batch, according to method using CellˆD software. The stained surface percentage (Surf %) for each treatment is compared to the untreated condition: P vs T.

Results:

TABLE 4

Percentage of surface positive to collagen I immunostaining in the papillary dermis for the concerned batches

| Image | Collagen I in the papillary surface (% surface): TD8 | Collagen I in the papillary surface (% surface): PD8 |
|---|---|---|
| 1 | 42.7 | 53.5 |
| 2 | 42.8 | 79.4 |
| 3 | 61.1 | 59.7 |
| 4 | 69.1 | 74.6 |
| 5 | 64.4 | 86.1 |
| 6 | 44.0 | 87.3 |
| 7 | 45.6 | 74.6 |
| 8 | 47.9 | 64.7 |
| 9 | 61.9 | 65.1 |
| Mean | 53.3 | 71.7 |
| Standard deviation | 10.6 | 11.7 |

Figure 2:
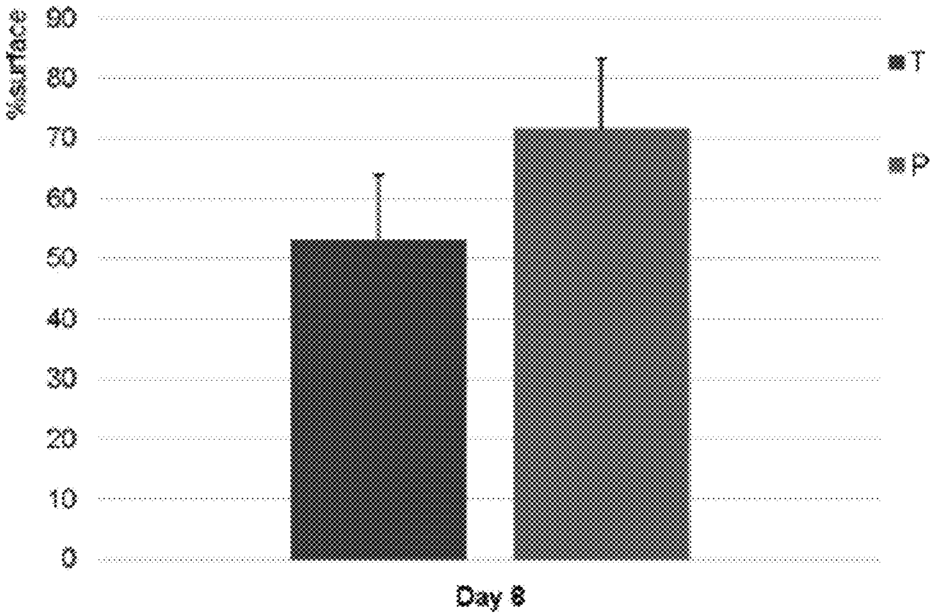
FIG. 2 illustrates the surface percentage positive to collagen I in the papillary dermis on day 8 for the blank batch T and the product P.

On day 8, On the blank batch TD8, the staining of collagen I represents 53.3% of the surface of the papillary dermis. The product P induces a significant increase of 35% illustrated in FIG. 2.

Conclusions:

The product P significantly stimulates the expression of collagen I on human living skin explants ex vivo after 8 days of treatment, so the plant derived active ingredient according to the invention induces a boost in collagen I synthesis.

Example 6: Total Polyphenol Assay

Product A was prepared was prepared according to example 2 except that leaves of *Cydonia oblonga* were note added, meaning that Product A only comprise oily extract of *Tilia platyphyllos.*

Product B was prepared was prepared according to example 2 except that leaves of *Tilia platyphyllos* were note added, meaning that Product A only comprise oily extract of *Cydonia oblonga.*

Product C is According to Example 2.

Those products compared to a simple macerate comprising 16% (w/w) of *Tilia platyphyllos* 4% (w/w) of *Cydonia oblonga* and 80% (w/w) of *Olea europaea* oil mixed together and macerated for 48 hours at 25° C.

Total phenols are determined using a method adapted from Singleton and Rossi (S. Ragaee, et al. Antioxydant activity and nutrient composition of selected cereals for food use. Science direct Food chem., 2006; 98:32-38), using Folin-Ciocalteu reagent as a color indicator.

The colorimetric properties of Folin-Ciocalteu reagent are modified when molecules are complexed, in particular when reacting with the —OH function of phenols (L. Catalano, et al. Polyphenols in olive mill waste waters and their depuration plant effluents: a comparison of the Folin-Ciocalteau and HPLC methods. Agrochimica., 1999; 43:193-20). This reaction results in the appearance of a dark blue color with a maximum absorption of around 725 nm. At this wavelength, and with reference to a calibration curve with known concentrations, it is possible to determine the concentration of total polyphenols in the samples to be analyzed.

| Sample | Total polyphenols in eq. Oleuropein (mg/kg of product) |
|---|---|
| Product A | 6 511 |
| Product B | 5 172 |
| Product C | 11 755 |
| Macerate | 230 |

Example 7: Assessment of the Activity of a Plant Derived Active Ingredient According to the Invention on the Anti-Radical Effect The CAT (Conjugated Autoxidizable Triene) assay is one of the spectrophotometric tests used to assess the total antioxidant capacity of samples. The CAT test measures a product's ability to scavenge free radicals, a sign of anti-aging activity. This test is well suited to oil-based products. It assesses a product's ability to block oxidative radical reactions. Using UV spectrophotometry, it measures the damage caused by free radicals on an oxidizable substrate. The presence of antioxidants in a tested product prevents free radicals from acting on the oxidizable substrate.

2,2'-azobis-2-amidinopropane dihydrochloride (AAPH) is used to generate reactive oxygen species (ROS) and tung oil is used as an oxidizable substrate. Trolox® (6-hydroxy-2,5,7,8-tetramethylchroman-2-carboxylic acid), a vitamin E analog, is used as an external reference and CAT results are expressed as Trolox Equivalents® per unit sample weight.

| Sample | CAT value (μmole trolox eq/kg of product) |
|---|---|
| Product A | 16 556 |
| Product B | 12 743 |
| Product C | 34 101 |
| Macerate | 363 |

The combination of two active ingredients in product A or B has an anti-radical effect at least 35 times greater than that of macerate.

The combination of the three active ingredients according to the invention results in 94 times more antioxidant activity than the corresponding macerate and a 16% synergistic increase in antioxidant activity as compared with the sum of the active ingredients taken two by two (product A+product B).

The invention claimed is:

1. A plant-derived active ingredient comprising:

(A) an extract from at least one plant of the gender *Olea,*

(B) an extract from at least one plant of the gender *Tilia*, and (C) an extract from at least one plant of the gender *Cydonia,* wherein the plant-derived active ingredient is obtained by an extraction method comprising:

a) mixing and impregnating the extract from at least one plant of the gender *Tilia* and at least one plant of the gender *Cydonia* with the extract from at least one plant of the gender *Olea* in an oily form at a temperature which is greater than the melting point of the extract from at least one plant of the gender *Olea,* b) heating to a temperature between 80 to 200° C., c) microdispersing the extract from at least one plant of the gender *Tilia* and the extract from at least one plant of the gender *Cydonia* into the extract from at least one plant of the gender *Olea*, and d) separating the oily content by centrifugation and/or filtration such that the plant-derived active ingredient is in an oily form.

2. The plant-derived active ingredient according to claim 1 wherein the at least one plant of the gender *Olea* is *Olea europaea.*

3. The plant-derived active ingredient according to claim 1 wherein the at least one plant of the gender *Tilia* is *Tilia platyphyllos.*

4. The plant-derived active ingredient according to claim 1 wherein the at least one plant of the gender *Cydonia* is *Cydonia oblonga.*

5. The plant-derived active ingredient according to claim 1 wherein a mass ratio between the extract from at least one plant of the gender *Tilia* and the extract from at least one plant of the gender *Cydonia* and the extract from at least one plant of the gender *Olea* is from 1:2 to 1:10.

6. The plant-derived active ingredient according to claim 1 wherein the plant derived active ingredient comprises one or more polyphenols in a concentration from 200 to 20,000 mg/kg.

7. The plant-derived active ingredient according to claim 1 wherein in the extraction method:

a) the mixing and impregnating is under an atmosphere which is depleted or essentially depleted in oxygen, b) the heating to a temperature between 80 to 200° C. is conducted in less than 10 minutes by means of micro-waves and under an atmosphere which is depleted or essentially depleted in oxygen, and c) the microdispersing is under an atmosphere which is depleted or essentially depleted in oxygen, by means of ultrasonic cavitation treatment, wherein step c) is implemented before, during or after step b).

8. A cosmetic composition comprising the plant-derived active ingredient according to claim 1.

9. The cosmetic composition according to claim 8 wherein the cosmetic composition further comprises at least one surfactant.

10. The plant-derived active ingredient according to claim 9 wherein the at least one surfactant is a water in oil surfactant selected from the group consisting of polyglyceryl-4 oleate, polyglyceryl-3 diisostearate, polyglyceryl-6 dioleate, polyglyceryl-3 caprate, glycerol stearate, and phospholipids, alone or in combination.

11. A drug composition comprising the plant-derived active ingredient according to claim 1.

12. The drug composition according to claim 11 wherein the drug composition further comprises at least one surfactant.

13. A method for increasing collagen synthesis in a subject comprising administering to the subject an effective amount of the plant-derived active ingredient according to claim 1.

14. The method according to claim 13 wherein the collagen is type I collagen.

15. Cosmetic method for decreasing skin ageing, increasing biomechanical properties of skin comprising firmness and/or elasticity, and/or reducing skin symptoms caused by oxidative stress and/or pollution and/or increasing the radiance of the skin said cosmetic method, comprising applying on the skin an effective amount of the plant-derived active ingredient according to claim 1.

* * * * *